United States Patent [19]

Gordon

[11] Patent Number: 4,784,940
[45] Date of Patent: Nov. 15, 1988

[54] QUANTITATION OF CANCER PROCOAGULANT ACTIVITY IN SERUM

[75] Inventor: Stuart G. Gordon, Denver, Colo.

[73] Assignee: Mesa Medical, Inc., Wheat Ridge, Colo.

[21] Appl. No.: 67,295

[22] Filed: Jun. 26, 1987

[51] Int. Cl.$^4$ .................. C12Q 1/56; G01N 33/48
[52] U.S. Cl. ............................................. 435/4; 435/13; 436/64; 436/69; 436/177; 436/813; 530/412
[58] Field of Search ................ 435/4, 13, 23, 24, 219, 435/813, 824, 825; 436/64, 69, 174, 177, 178, 813; 530/412, 420, 427

[56] References Cited

U.S. PATENT DOCUMENTS

| | | | |
|---|---|---|---|
| 4,447,545 | 5/1984 | DeFazio | 436/64 |
| 4,461,833 | 7/1984 | Gordon | 435/219 |
| 4,622,389 | 11/1986 | Nagasawa | 435/13 |
| 4,678,757 | 7/1987 | Rapkin | 435/13 |

OTHER PUBLICATIONS

Gordon et al.; J. Natl. Cancer Inst., vol. 62, No. 4, Apr. 1979, pp. 773–776.
Gordon et al.; J. Clin. Invest., vol. 67, Jun. 1981, pp. 1665–1671.
Falanga et al.; Biochemistry, 24, 5558 (1985); pp. 5558–5567.

Primary Examiner—Kenneth M. Schor
Attorney, Agent, or Firm—Dean P. Edmundson

[57] ABSTRACT

Methods and techniques are described for detecting the presence of cancer procoagulant activity in blood serum. The method provides a means of distinguishing persons or animals having cancer from those who do not have cancer. The method involves techniques for processing serum such that the activity of cancer procoagulant can be measured while the activity of other coagulation enzymes in the serum is minimized or eliminated. Then the serum can be analyzed for cancer procoagulant activity.

12 Claims, 1 Drawing Sheet

QUANTITATION OF CANCER PROCOAGULANT ACTIVITY IN SERUM

FIELD OF THE INVENTION

This invention relates to detection of cancer procoagulant. More particularly, this invention relates to detection of cancer procoagulant in animals and humans. Even more particularly, this invention relates to methods and techniques for preparing a serum sample in a manner such that cancer procoagulant activity can be measured.

BACKGROUND OF THE INVENTION

Modern medicine has provided various techniques and methods for treating cancer patients. However, before any of such techniques or methods can be used for treatment of cancer patients, it is first necessary to detect the cancer in the patient. Experience has shown that the earlier the cancer is detected the greater the likelihood that the cancer can be effectively treated (e.g., by surgery, chemotherapy, or other known procedures).

An increased incidence of vascular thrombosis and disseminated intravascular coagulation associated with malignant disease has been known for a long time. It has also been known that there is increased removal of fibrinogen from the circulation of experimental animals and humans with cancer, and much of this fibrin is deposited in and around the solid tumor.

Fibrin deposition is thought to promote tumor growth by providing a supporting network or "cocoon" of fibrin in which new cells can grow. Alternatively, it may protect the malignant cells from the host defense system. Fibrin is associated with blood-borne malignant cells that are potentially metastatic. This fibrin may facilitate clumping of tumor cells with other blood cells such that the tumor cell embolus will lodge in small capillaries of organs susceptible for tumor growth (e.g., the lung).

The administration of anticoagulants and fibrinolytic agents to experimental animals decreases tumor growth and metastasis. It has also been demonstrated that malignant tissue has increased procoagulant and fibrinolytic activity.

Cancer procoagulant has been purified and characterized from malignant tissue. It is not present in normally differential cells and tissue. See, for example, *Isolation and Characterization of Cancer Procoagulant: A Cysteine Proteinase From Malignant Tissue*, Biochemistry, 24, 5558 (1985); *A Factor X-Activating Cysteine Protease From Malignant Tissue*, J. Clin. Invest., Volume 56, pp. 1665-1671 (June, 1981); and *Comparison of Procoagulant Activities In Extracts of Normal and Malignant Human Tissue*, J. Nat'l. Cancer Inst., Vol. 62, No. 4 (April, 1979); each of which is incorporated herein by reference. See also my U.S. Pat. No. 4,461,833 which describes techniques for purifying cancer procoagulant from animal tissue extract, incorporated herein by reference.

Cancer procoagulant is a cysteine proteinase with a molecular weight of 68,000 that initiates coagulation by directly activating factor X in the coagulation cascade. It is physically, chemically and enzymatically distinct from other coagulation enzymes. In particular, it is distinct from tissue factor. Tissue factor is a membrane lipoprotein that initiates coagulation via factor VII and is present in both normal and malignant cells.

The activation of factor X by cancer procoagulant can be more easily understood with reference to FIG. 1, which is a schematic diagram showing the activation of both the intrinsic and extrinsic pathways. Activation of the intrinsic pathway by surface contact causes factor XII to form factor XIIa, which, acting through the proteolytic conversions of factors XI and IX, results in an active complex composed of factor IXa, factor VIII, calcium and phospholipid, all of which facilitates the proteolytic activation of factor X to Xa. Tissue damage facilitates the exposure of tissue factor which, when it binds to factor VIIA, forms a very potent activator of factor X. Cancer procoagulant is a cysteine proteinase that directly activates factor X. Russell's Viper Venom (R.V.V.) is a serine proteinase that directly activates factor X and has been used herein as a control activator of the assay. The conversion of factor X, in turn, by either intrinsic or extrinsic pathways, activates prothrombin (II) to thrombin (IIa) in the presence of calcium, phospholipid, and factor V. Thrombin converts fibrinogen to fibrin and activates factor XIII which facilitates fibrin monomer polymerization.

There has not heretofore been provided a method or technique for detecting the presence of cancer procoagulant activity in blood serum.

SUMMARY OF THE PRESENT INVENTION

In accordance with the present invention there is provided a method for detecting and quantitating cancer procoagulant activity in blood serum. In another aspect the invention involves a technique for analyzing blood serum to distinguish animals and humans having cancer from those without cancer. In another aspect the invention involves a method for preparing a serum sample to permit analysis thereof for cancer procoagulant.

The techniques of the invention involve:

(a) obtaining a blood sample from an animal or human to be tested;

(b) removing essentially all cellular material from the sample;

(c) disassociating the cancer procoagulant from other proteins present in the sample;

(d) denaturing the proteins other than the cancer procoagulant;

(e) separating the denatured proteins from the cancer procoagulant; and (f) analyzing the sample for the presence of cancer procoagulant activity.

Using the techniques of this invention it is possible to separate and detect the presence of cancer procoagulant activity in serum. This procedure is relatively easy and rapid to use.

It also serves as a means of screening animals and humans to determine whether they may have cancer. The procedure is also useful for monitoring progress of cancer patients undergoing treatment for cancer.

The techniques of the invention do not require expensive and sophistocated laboratory equipment or procedures.

DETAILED DESCRIPTION OF THE INVENTION

Figure 1:
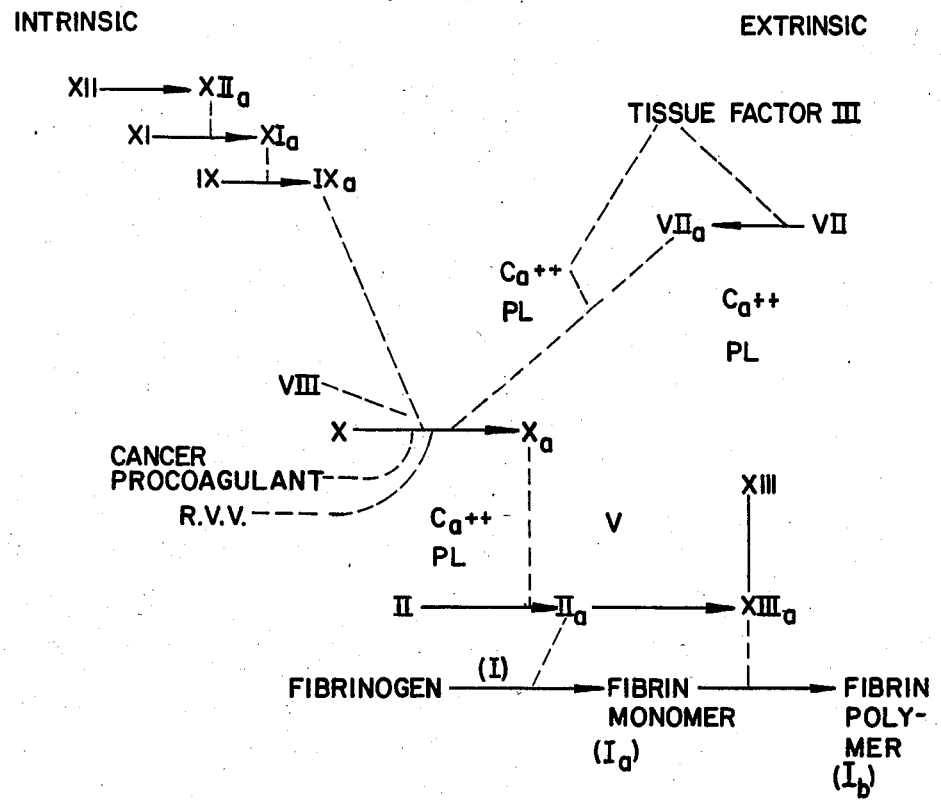
FIG. 1 is a schematic diagram showing activation of factors, for both intrinsic and extrinsic pathways.

In the techniques of the present invention it is first necessary to remove essentially all cellular material and cellular debris from the sample to be tested. Although an ordinary centrifuge may be used to remove most cellular material, it is not sufficient to remove essentially all cellular material and cellular debris. Even multiple centrifugations are not sufficiently effective in removing essentially all cellular material and debris.

Centrifuging at 100,000 xg. may be more useful in removing undesired materials from the serum. Various filters or screens may also be useful in removing cellular material and debris. For example, after a sample has been centrifuged, a filter tube may be inserted into the serum at the top of the blood tube. The serum is forced through a filter and into the interior of the tube.

A more preferred procedure for removing cellular material and debris involves the use of a serum separator tube of the type which is commercially available from Becton-Dickinson under the name "SST". This type of serum separator tube includes a wax plug which migrates to the interface between the serum and the cellular blood clot during centrifugation. This separator tube is very effective in providing separation of the cellular material and debris from the fluid component of the serum.

Plasma or serum from animals and humans contains a number of enzymes that can either activate or enhance the coagulation activity of a blood sample. In the techniques of this invention, the cancer procoagulant must be disassociated from the other proteins present in the sample. A preferred technique for effecting this is to add to the serum sample (from which essentially all cellular material has been removed) a buffer solution containing DMSO (dimethylsulfoxide), followed by a short period of incubation (e.g., 5 minutes at room temperature, e.g., 25° C.).

A preferred buffer solution is 20 mM Veronal buffer (sodium barbital; pH 7.4). This buffer is commercially available (from Sigma Chemical Co.) and it works well. Other useful buffers of similar types include Hepes (commercially available from Cal Biochem) and Tris (commercially available from Sigma Chemical Co.). These types of buffers do not bind divalent ions in the serum.

Preferably the relative amounts of serum, buffer, and DMSO are as follows:

| | |
|---|---|
| serum | 60 microliters |
| DMSO | 45 microliters |
| Veronal buffer | 45 microliters |

Using the above procedure the cancer procoagulant present in the serum sample is dissociated from the other proteins without denaturing any of the proteins nn the sample.

The DMSO reduces the polarity of the serum. It's dielectric constant is about one-half that of water. It is able to reduce ionic interaction between molecules in the sample, and it does not denature the proteins. Other such materials may also be used provided that they function in a similar manner and do not denature the proteins.

Then an extraction mixture comprising aluminum hydroxide gel and potassium cyanide is added to the sample. A preferred extraction mixture is as follows:

| | |
|---|---|
| aluminum hydroxide gel - 1:5 dilution in 20 mM Veronal buffer containing: | |
| potassium cyanide (KCN) | 4 mM |
| ferrous chloride ($FeCl_2$) | 4 mM |
| magnesium chloride ($MgCl_2$) | 4 mM |
| manganese chloride ($MnCl_2$) | 4 mM |
| zinc chloride ($ZnCl_2$) | 4 mM |

Preferably 50 microliters of this extraction mixture is added to the serum sample, after which the sample is heated to 55° C. for 5 minutes to denature all proteins in the serum other than the cancer procoagulant. In other words, this procedure selectively denatures the other coagulation factors and antiproteinase in the serum.

The potassium cyanide (KCN) keeps the active site (SH) on the cancer procoagulant from being oxidized to $S_2$.

The aluminum hydroxide gel serves as a binding agent to take out vitamin K dependent coagulation factors. Barium hydroxide may extract these same factors in a similar fashion.

After the extraction mixture has been added and the sample has been heated as explained above, the sample is centrifuged for four minutes in a microfuge at 13,000 xg.

The supernatant is then analyzed for cancer procoagulant activity by means of the standard recalcification clotting time assay using a conventional fibrometer. This procedure involves placing 0.1 ml. of citrated, and genetically deficient in factor VII, plasma in a coagulation cup and warming it to 37° C. for one minute. The sample supernatant (0.1 ml.) is added to the cup and the reaction is initiated by adding 0.1 ml. of pre-warmed 30 mM calcium cloride (in water). The clotting time is then measured in seconds. Other conventional means for measuring clotting times may also be used, if desired.

Blank samples are measured to determine the clotting time of the plasma without activation by substituting the buffer (DMSO plus KCN and the divalent ions in Veronal buffer) for the serum sample. Russell's Viper Venom (RVV) is used as a coagulation standard in the assay because it is known to directly activate factor X and therefore it mimics cancer procoagulant activity.

Dilutions of commercial RVV (from Sigma) are prepared by diluting the RVV stock solution (prepared according to the supplier's printed instructions). Four dilutions of RVV are prepared in Veronal buffer, i.e., 1:1,000; 1:10,000; 1:100,000; and 1:1,000,000. These standards are then added to the reaction mixture in place of the serum samples, after which the clotting times are measured. The results are used to calibrate the assay plasma.

There is a log-linear relationship between the clotting time and the RVV concentration when different concentrations of RVV are added to factor VII deficient assay plasma.

Serum samples were spiked with known amounts of cancer procoagulant and then tested in accordance with the principles of this invention. Linearity of the cancer procoagulant activity in the serum was confirmed.

The characteristics of the procoagulant activity in the serum was tested to confirm that it was the same as that of cancer procoagulant. The activity was inhibited by 0.1 mM mercuric chloride (a common inhibitor of cysteine proteinase). Serum samples spiked with 20, 40, and 60 microliters of cancer procoagulant were first extracted and analyzed in accordance with the techniques of the invention without inhibitor present.

Then spiked serum samples were treated with the mercuric chloride, extracted and analyzed. All of the samples containing mercuric chloride were inhibited and had no more activity than the serum by itself (without cancer procoagulant present).

In another study of a serum sample spiked with cancer procoagulant, the activity was reduced by addition of mercuric chloride from 29% activity to that of the serum extract alone. In addition, the extract samples were assayed in factor VII deficient human plasma; tissue factor is inactive in factor VII deficient plasma. The extract samples were assayed in the immunoassay for cancer procoagulant and the presence of cancer procoagulant antigen was confirmed.

The techniques of the invention are effective in preparing serum samples so that the presence of cancer procoagulant can be detected and measured with very good accuracy. The techniques thus provide a means for simply detecting cancer in animals and humans.

What is claimed is:

1. A method for detecting cancer procoagulant activity in blood serum comprising the steps of:
   (a) obtaining a blood sample of animal or human blood;
   (b) removing essentially all cellular material from said sample;
   (c) dissociating said cancer procoagulant from other proteins present in said sample;
   (d) denaturing said other proteins in said sample without denaturing said cancer procoagulant;
   (e) separating said other proteins from said cancer procoagulant; and
   (f) analyzing said sample for said cancer procoagulant by determining cancer procoagulant activity.

2. A method in accordance with claim 1, wherein said blood sample is from a human.

3. A method in accordance with claim 1, wherein said blood sample is from an animal.

4. A method in accordance with claim 1, wherein said cellular material is removed from said sample by means of a separator tube.

5. A method in accordance with claim 1, wherein DMSO and a buffer solution are added to said sample to dissociate said cancer procoagulant from said other proteins.

6. A method in accordance with claim 1, wherein an extraction mixture is added to said sample, wherein said extraction mixture comprises aluminum hydroxide gel and potassium cyanide.

7. A method for detecting cancer procoagulant activity in blood serum, said method comprising the steps of:
   (a) obtaining a blood sample of animal or human blood;
   (b) removing essentially all cellular material from said sample;
   (c) adding to said sample a buffer solution containing DMSO;
   (d) incubating said sample at room tmperature;
   (e) adding to said sample an extraction mixture comprising aluminum hydroxide gel and potassium cyanide;
   (f) heating said sample to a temperature of about 55° C. for a time sufficient to denature coagulation factors and anti-proteinase without denaturing said cancer procoagulant;
   (g) centrifuging said sample; and
   (h) analyzing the supernatant of said sample for said cancer procoagulant by determining cancer procoagulant activity.

8. A method in accordance with claim 7, wherein said cellular material is removed from said blood sample by means of a separator tube.

9. A method in accordance with claim 7, wherein said blood sample is obtained from an animal.

10. A method in accordance with claim 7, wherein said blood sample is obtained from a human.

11. A method in accordance with claim 7, wherein said buffer solution comprises Veronal buffer.

12. A method in accordance with claim 7, wherein said extraction mixture further includes ferrous chloride, magnesium chloride, manganese chloride, and zinc chloride.

* * * * *